US010695525B2

(12) United States Patent
Borgonjon et al.

(10) Patent No.: US 10,695,525 B2
(45) Date of Patent: Jun. 30, 2020

(54) VALVE FOR CONTROLLING GAS FLOW

(75) Inventors: Dirk Borgonjon, Kapellen (BE); Philip Hendrickx, Berchem (BE)

(73) Assignee: OXYPOINT NV, Antwerp (BE)

( * ) Notice: Subject to any disclaimer, the term of this patent is extended or adjusted under 35 U.S.C. 154(b) by 76 days.

(21) Appl. No.: 14/116,934

(22) PCT Filed: May 10, 2012

(86) PCT No.: PCT/IB2012/052329
§ 371 (c)(1),
(2), (4) Date: Nov. 11, 2013

(87) PCT Pub. No.: WO2012/153293
PCT Pub. Date: Nov. 15, 2012

(65) Prior Publication Data
US 2014/0076321 A1   Mar. 20, 2014

(30) Foreign Application Priority Data

May 10, 2011   (BE) .................................. 2011/0289

(51) Int. Cl.
*A61M 16/20*  (2006.01)
*A61M 16/12*  (2006.01)
*A61M 16/06*  (2006.01)

(52) U.S. Cl.
CPC ........ *A61M 16/20* (2013.01); *A61M 16/0666* (2013.01); *A61M 16/0677* (2014.02);
(Continued)

(58) Field of Classification Search
CPC .................. A61M 16/00; A61M 16/20; A61M 16/201–16/208; A61M 16/0677; A62B 9/02; A62B 18/10; B63C 11/14; B63C 11/16; B63C 11/18; F16K 21/00; F16K 21/04

See application file for complete search history.

(56) References Cited

U.S. PATENT DOCUMENTS 4,932,402 A   6/1990  Snook et al.
5,038,770 A   8/1991  Perkins
(Continued)

FOREIGN PATENT DOCUMENTS

EP   1325762 A1   7/2003
FR   2813799 A1   3/2002
(Continued)

OTHER PUBLICATIONS

International Search Report for corresponding PCT Application No. PCT/IB2012/052329, dated Sep. 17, 2012.

*Primary Examiner* — Peter S Vasat
(74) *Attorney, Agent, or Firm* — Workman Nydegger

(57) ABSTRACT

A gas valve is arranged for controlling the flow of medical gas for oxygen therapy in case of spontaneous breathing. An embodiment of the gas valve contains a connection component to connect the gas valve to an external supply such as for example an external supply network for medical gases at a pressure lower than 50 bars. The gas valve may contain a regulating system configured to select and supply a pulsating or continuous flow of medical gas in which the regulating system contains a flow rate regulator to controllable set the flow rate of the continuous flow.

20 Claims, 5 Drawing Sheets

(52) U.S. Cl.
CPC .......... *A61M 16/12* (2013.01); *A61M 16/125* (2014.02); *A61M 16/201* (2014.02); *A61M 2202/0208* (2013.01)

(56) References Cited

U.S. PATENT DOCUMENTS

| | | | | |
|---|---|---|---|---|
| 5,720,276 | A * | 2/1998 | Kobatake | A61M 16/00 128/204.18 |
| 5,911,219 | A * | 6/1999 | Aylsworth | A61M 16/20 128/203.24 |
| 6,032,667 | A | 3/2000 | Heinonen | |
| 6,186,477 | B1 | 2/2001 | McCombs et al. | |
| 6,427,690 | B1 * | 8/2002 | McCombs | A61M 16/00 128/204.23 |
| 6,612,307 | B2 | 9/2003 | Byrd | |
| 2002/0073998 | A1 | 6/2002 | Byrd | |
| 2003/0127099 | A1 | 7/2003 | Meneuvrier et al. | |
| 2005/0192538 | A1 * | 9/2005 | Voege | A61M 16/0666 604/167.03 |
| 2006/0219245 | A1 * | 10/2006 | Holder | A61M 16/0666 128/204.26 |
| 2007/0017520 | A1 | 1/2007 | Gale et al. | |
| 2008/0173304 | A1 | 7/2008 | Zaiser et al. | |
| 2008/0190429 | A1 * | 8/2008 | Tatarek | A61M 16/00 128/204.23 |
| 2009/0205660 | A1 | 8/2009 | Thomson et al. | |
| 2011/0048423 | A1 * | 3/2011 | Leffel | A61M 16/20 128/205.24 |
| 2012/0085348 | A1 | 4/2012 | Chalvignac et al. | |

FOREIGN PATENT DOCUMENTS

| | | |
|---|---|---|
| GB | 2430159 A | 3/2007 |
| WO | 1999022796 A1 | 5/1999 |
| WO | 2010141983 A1 | 12/2010 |

* cited by examiner

VALVE FOR CONTROLLING GAS FLOW

FIELD OF THE INVENTION

In general, this invention concerns systems for the supply of oxygen, for example to patients in hospitals. More specifically, the present invention relates to a gas valve for the supply of oxygen, a system containing such a gas valve, and the use of such a gas valve for controlling the gas flow, e.g. oxygen gas flow intended for patients in hospitals.

BACKGROUND OF THE INVENTION

The use of gases in medical applications is widespread. One of the gases often administered to patients for medical reasons is oxygen. In view of the fact that administering oxygen is often essential for preventing damage to tissue, avoiding life-threatening situations or saving a patient from a life-threatening situation, hospitals distribute oxygen using a pipeline network up to the bed of nearly each patient. The conventional form of administering oxygen through a pipeline network is in a continuous manner. A flow meter can be set to the flow rate that the patient needs (1 l/min up to 15 l/min continuously or higher). This way the oxygen flows continuously from the source to the patient via a nasal cannula during inhaling and exhaling. The flow meter is plugged into the low-pressure oxygen socket (usually between 3.6 and 5.5 bars) on the wall behind the patient's bed. A moisturizer can be attached to the bottom side to prevent drying up of the nasal mucous membrane.

The lungs can only utilise the first phase of inhalation to exchange oxygen with the blood circulation. It is clear that oxygen can no longer be 'consumed' during the expiration phase (exhalation). However, during the last phase of inhalation too, only the large bronchial tube that does not participate in the diffusion process of oxygen is filled. Gas valves for the pulsating supply of medical gases are based on this principle: oxygen is purposefully administered during the first phase of inhalation by the patient. This way a maximum oxygen intake is achieved and the oxygen that is not used is minimised. This results in savings without impacting the oxygen therapy.

Various gas valves have been developed during the past 20 years which are based on the principle of discontinuous oxygen administration in order to increase the mobility of patients that use oxygen cylinders at home and/or to increase the autonomy of recipients. After all, the use of gas valves for mobile patients saves oxygen, which results in a lower consumption and consequently creating longer autonomy, i.e. 3 to 5 times longer than the autonomy achieved with continuous administration.

Most gas valves are based on a regulating system in which nasal inhalation activates the gas valve. The underpressure activates and opens an oxygen valve through which an oxygen pulse (aka bolus) is generated. Detecting the inhalation and supplying the oxygen occurs by means of a nasal cannula. A nasal cannula can be a one-channel system (detection and supply occur through the same channel) or a two-channel system in which one channel is used for detecting the inhalation and the other channel is used for supplying the oxygen.

EP1325762 describes a one-channel system for the supply of medical gases. The system provides an oxygen bolus in case of detecting inhalation and provides a period of delay following the oxygen bolus in order to avoid a redundant double oxygen pulse.

U.S. 2008/0173304 A1 describes a pneumatic valve for medical gases that combines the typical advantages of operating a one-channel nasal cannula and a two-channel nasal cannula. The pneumatic medical gas valve generates a gas pulse based on the detection of nasal inhalation and prevents generating a double pulse by applying a pneumatically induced delay.

U.S. 2007/0017520 A1 describes a device for administering oxygen in which gas is released in case of inhalation and in which the gas flow is interrupted by a dedicated pneumatic system.

FR2813799 A1 describes a gas valve for oxygen in which a continuous flow and a pulsating administration are possible. The gas valve consists of two channels to the patient: one channel takes care of supplying the oxygen and the other channel ensures the detection of inhalation. Furthermore, the gas valve has a pressure regulator so that the gas valve can be connected to a gas cylinder under high pressure.

U.S. Pat. No. 4,932,402 describes a gas valve that provides a user-specific oxygen supply based on the measured breathing of the patient using an electronic control. Moreover, the system is customised to switch to a continuous oxygen flow in case of power failure or poor operation.

U.S. Pat. No. 5,038,770 describes another valve that has a safeguard in case the control system for pulsating supply fails or if there is a power failure.

Most of the aforementioned systems are suitable for home use in which a gas cylinder is used.

Hospitals have to cope with a large circulation of patients. That means that systems with a complex adjustment to the patient's individual needs are time-consuming for the patient and for the medical staff. In addition, hospitals have a large variety of medical gas therapies that are used even during the treatment of one and the same patient. This differs significantly from home devices used by an individual patient in which the patient usually sets the correct adjustment only once (or a limited number of times) and after that, he/she can usually use the same adjustment. In addition, the current technology does not enable generating a pulse dosage of more than 6 l/min. The result is that the available economizer valves are not suitable for all patients and consequently, cannot be used efficiently in hospitals.

Therefore, a valve for checking the flow of medical gas that can be used effectively in specific institutional environments such as hospitals is required. In addition, there is a need for a medical gas flow controlling valve that enables a larger flow of medical gas (e.g., more than 6 l/min).

SUMMARY OF THE INVENTION

It is an object of embodiments according to the present invention to provide a valve for controlling the gas flow of medical gases that can be used effectively in hospitals as well as a method for its use.

It is an advantage of at least some embodiments of the present invention that it allows an efficient switch between various settings of the gas valve, enabling the use of the valve in frequently changing situations applicable to hospitals, for example.

It is an advantage of at least some embodiments of the present invention that it allows the production of a gas valve that enables setting a large gas flow (e.g., a gas flow with a flow rate of more than 6 l/min).

It is an advantage of embodiments of the present invention that it allows simple adjustment of the therapy, for example, as a result of a different process of rehabilitation or as a result of the patient's need for another type of therapy.

It is an advantage of embodiments of the present invention that it provides functioning of the gas valve as an economizer valve: this can result in a considerable reduction of the quantity of gas used.

It is an advantage of at least some embodiments of the present invention that it provides optimising the use of medical gases: this can result in reduced consumption of medical gases (average is more than 50% e.g., more than 70% or 80%) compared with the use of a continuous gas flow.

It is an advantage of at least some embodiments of the present invention that it poses fewer burdens on the environment due to the potential reduction in the production of medical gases and the reduction in transport time of medical gases as a result of the reduced consumption of oxygen.

It is an advantage of at least some embodiments of the present invention that it provides a more fire-proof environment because fewer unused medical gases such as oxygen are distributed in the rooms.

It is an advantage of embodiments of the present invention that it allows enabling an easy switch from continuous flow to pulsating supply and vice versa.

It is an advantage of at least some embodiments of the present invention that it allows enabling continuous supply with high flow rates in addition to a pulsating supply. An additional advantage is that such a continuous supply can occur with high accuracy.

It is an advantage of at least some embodiments of the present invention that it provides initial operation of the gas valve (i.e., every time it is switched on after closing the gas valve or after connecting to the gas supply network) in the mode of pulsating supply so that a saving is achieved, even if the medical staff or the user does not adjust the valve.

It is an advantage of at least some embodiments of the present invention that the pulsating mode of the gas valve can operate independently of the settings for the continuous mode of the gas valve.

It is an advantage of at least some embodiments of the present invention that a safeguarding element is built into the gas valve so that only connecting to a specific gas connection for a specific medical gas is possible.

It is an advantage of at least some embodiments of the present invention that a simple switch to continuous flow is possible, for example, if the pulsating supply makes too much noise when falling asleep or if the patient breathes too heavily through his/her mouth (resulting in insufficient underpressure of the economizer system to activate the oxygen pulse) or at critical moments in which the doctor wishes to switch to continuous flow or to higher flow rates.

The aforementioned objective is achieved by a device and a method according to the embodiments of the current invention.

The current invention relates a gas valve for controlling the flow of medical gas for oxygen therapy in case of spontaneous breathing in which the gas valve comprises a connection component for connecting the gas valve to an external supply and a regulating system that is configured for selecting and supplying a pulsating flow of medical gas or a continuous flow of medical gas, and wherein the regulating system has a flow-rate regulator for controllably setting the flow rate of the continuous flow of medical gas.

It is an advantage of at least some embodiments according to the present invention that an economizer system for administering medical gases (e.g., oxygen) is provided that is suitable for use in specialised institutions such as hospitals, old age homes and nursing homes, so that these specialised institutions can optimise the administration of medical gases in the first phase of inhalation. As a result, the use of these economizer systems (aka valves with supply-on-demand) achieves considerable saving of medical gases in specialised institutions.

It is an advantage of at least some embodiments according to the present invention that an economizer system is provided that is specifically adapted to the needs of stationary use (e.g., hospital beds).

It is an advantage of at least some embodiments of the present invention that additional moisturizing systems can be avoided by providing a setting for pulsating flow, reducing the risk of infections. The external supply of some embodiments can be a supply network for medical gases with a pressure lower than 50 bars or it can be a gas cylinder.

The flow rate regulator can be equipped minimally for the controllable setting of the flow rate of the continuous flow with a range of 2 l/min up to 8 l/min.

It is an advantage of at least some embodiments according to the present invention that there is a controllable flow even for flow rates that are higher than 6 l/min. The flow rate regulator can be equipped minimally for the controllable setting of the flow rate of the continuous flow with a range of 2 l/min up to more than 10 l/min, while some embodiments have a range of more than 15 l/min or even more than 25 l/min. Other examples of ranges in which valves (e.g., valves for paediatric applications) can be controllably set are 0-200 cc/min, 0-1 l/min, 0-3 l/min and 1-2 l/min, for example.

It is an advantage of at least some embodiments of the present invention that a high flow rate can be provided in a controllable manner so that the gas valve can also be used for more critically ill patients.

In view of the fact that specialised institutions have to cope with a quick turnover of patients, it is an advantage to use gas valves both for less critically ill patients and more critically ill patients.

The flow rate regulator can be a flow rate meter such as a flow meter. The gas valve can be configured so that the flow rate regulator does not impact the flow of medical gas if the regulating system is set to pulsating flow.

It is an advantage of at least some embodiments of the present invention that the gas valve can operate in pulsating mode, independent of the status of the flow rate regulator, so that the medical staff or user is not required to execute specific actions.

The regulating system can consists of a first sub-regulating system for supplying a pulsating flow and a second sub-regulating system for supplying a continuous flow in which the flow rate regulator is part of the second sub-regulating system and in which the gas valve is configured in such a way that the first sub-regulating system and the second sub-regulating system are in parallel gas channels.

It is an advantage of at least some embodiments according to the present invention that, if the gas valve is used in the pulsating position, the status of the second sub-regulating system does not affect the delivered gas supply.

The gas valve can be configured so that the regulating system is in a mode of pulsating gas flow at the start of the flow.

It is an advantage of at least some embodiments according to the present invention that the gas valve can start standard in pulsating flow, providing a saving regimen in case the valve is not adjusted.

For activating the second sub-regulating system, an accessory selection system might need to be activated. It should be de-activated when the continuous flow is interrupted.

It is an advantage of at least some embodiments according to the present invention that additional actions should be undertaken to generate the continuous flow in order to avoid the spontaneous and superfluous use of the continuous flow setting.

The gas valve can operate mechanically and pneumatically. An additional advantage is that powering for the valve's operation (e.g., by a battery) can be avoided, which reduces costs and maintenance.

The regulating system can enable the selection of the flow type via a click system. It is an advantage of embodiments of the present invention that the gas valve can be switched from pulsating flow to continuous flow in a simple manner (via one click or a few clicks, for example).

Furthermore, the regulating system can be configured to select and supply various types of pulsating flows.

It is an advantage of embodiments of the present invention that the gas valve enables the selection of a pulsating flow that corresponds with a certain flow rate.

The gas valve can be adjusted, e.g. by adjusting the operation of the regulating system for supplying the pulsating flow, to close the pulsating flow based on a pre-determined signal, for example, if underpressure is lacking, which indicates that nasal inhalation is missing.

The gas valve can include a closing mechanism to close the pulsating flow and the continuous flow on the basis of a pre-determined signal.

It is an advantage of at least some embodiments of the present invention that the gas valve can be a valve with supply-on-demand, which can provide a stop function for the pulsating flow and the continuous flow. This can be useful in specialised institutions, for example, when the patient is examined. The pre-determined signal can be the lack of underpressure over a certain period (e.g., if the patient removes the nasal cannula through which the flow occurs) and/or a one-way valve signal 'present' or 'missing' in the system.

The gas valve can be equipped with a one-channel lead-through for connecting a one-channel nasal cannula for supplying the medical gas to the patient.

It is an advantage of embodiments of the present invention that the gas valve can operate together with a one-channel nasal cannula, which are less expensive.

The gas valve can be equipped with a two-channel lead-through for connecting a two-channel nasal cannula for supplying the medical gas.

It is an advantage of embodiments of the present invention that the gas valve can operate together with more sophisticated two-channel nasal cannulas, which provide more flexibility and control.

The valve can also include a system cut-off valve for closing the flow, which is activated by disconnecting the one-channel nasal cannula from the one-channel lead-through or the two-channel nasal cannula from the two-channel lead-through.

The flow rate regulator can enable a flow rate of medical gas of more than 15 l/min or more than 25 l/min.

The flow rate regulator can be adjusted to set and control the flow rate of the continuous supply to one of a few pre-determined flow rates.

The flow rate regulator can be adjusted to set and control continuously the flow rate of the continuous supply.

The regulating system can be adjusted to supply a pulsating flow of medical gas with a flow rate of more than 6 l/min during pulsation.

The current invention also relates to a kit of parts, including the aforementioned gas valve and a nasal cannula for the administration of medical gas in which the nasal cannula can be connected to the gas valve.

In addition, the current invention also relates to the use of the aforementioned gas valve for checking the flow of a medical gas.

Specific and preferred aspects of the invention are included in the attached independent and dependent conclusions. Characteristics of the dependent conclusions can be combined with the characteristics of the independent conclusions and with characteristics of other dependent conclusions as indicated and not solely as explicitly stated in the claims.

SHORT DESCRIPTION OF THE FIGURES

FIG. 3 illustrates a schematic representation of a gas valve according to an embodiment of the present invention, which includes a parallel gas lead-through and which has the regulating system for pulsating flow in one lead-through and the regulating system for continuous flow in another lead-through.

Figure 1:
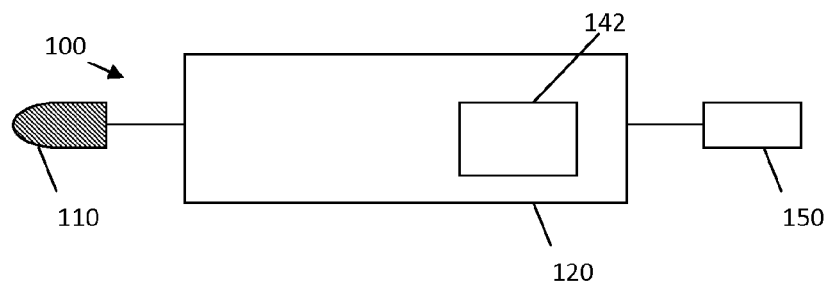
FIG. 1 illustrates a schematic representation of a gas valve according to an embodiment of the present invention.

The figures are only schematic and are not limiting. For illustrative purposes, the figures might exaggerate the dimensions of some components and these dimensions are not shown on scale. The dimensions and relative dimensions do not necessarily correspond with the ones of the practical embodiments of the invention.

Reference numbers in the conclusions may not be interpreted to limit the scope of protection of rights.

DETAILED DESCRIPTION OF THE ILLUSTRATIVE EMBODIMENTS

The current invention is described while referring to specific embodiments and to certain figures, but the invention is not limited by these referrals. The invention is only limited by the claims.

It should be noted that the terms "comprise" and "contain" as used in the claims should not be interpreted as 'limiting to the means described below'. These terms do not exclude other elements. These should be interpreted as specifying the presence of the stated and referred features, values, steps or components, but do not exclude the presence or addition of one or more other features, values, steps, components or combinations/groups of these. Therefore, the scope of the expression 'an arrangement comprising means A and B' should not be limited to arrangements only consisting of components A and B. Regarding the current invention, it means that A and B are the only relevant components of the arrangement.

Referral throughout this specification to 'one embodiment' or 'an embodiment' means that a specific feature, structure or characteristic described in relation to the embodiment is included in at least one embodiment of the current invention. Therefore, all appearances of expressions 'in one embodiment' or 'in an embodiment' at several places throughout this specification do not necessarily refer to the same embodiment, but they can refer to the same embodiment. Furthermore, the specific features, structures or characteristics can be combined in any suitable manner (as may be clear to a professional on the basis of this notification) in one or more embodiments.

Similarly, it should be understood that sometimes the description of sample embodiments of the invention groups various features of the invention in a single embodiment, figure or its description for the purpose of streamlining the disclosure or assisting in understanding one or more different inventive aspects. This method of disclosure should not be interpreted in any way as a representation of an intention that the invention requires more features than are mentioned explicitly in each conclusion. Rather (as the following conclusions represent) inventive aspects are in fewer than all the features of a single disclosed embodiment. Therefore, the claims that follow the detailed description are explicitly included in this detailed description, with each individual claim as a separate embodiment of this invention.

In addition—while some embodiments described in this detailed description contain some features, but do not contain other features included in other embodiments—combinations of features of different embodiments are intended as within the scope of the invention and constitute these different embodiments as should be understood by the person skilled in the art. For example, the following claims can use any of the described embodiments in any combination.

It should be noted that the use of specific terminology in describing certain features or aspects of the invention should not be interpreted to imply that the terminology is redefined to be limited to specific characteristics of the features or aspects of the invention with which this terminology is linked.

In the embodiments of the present invention, wherever reference is made to 'flow' or 'gas flow', the reference is to the flows of gas in which case the reference can be to a pulsating flow of gas as well as to a continuous flow of gas.

In the embodiments of the current invention, wherever reference is made to 'flow rate', the reference is to the variable that expresses the volume of gas that flows through the system per time unit.

In the embodiments of the present invention, wherever reference is made to 'oxygen therapy', reference is to a therapy in which oxygen is added to achieve a concentration of oxygen that is higher than the standard concentration in the ambient air.

In embodiments of the current invention, pulsating gas supply is activated preferably by breathing i.e., inhalation can typically trigger a gas pulse while during exhalation no gas pulse is provided.

Embodiments of the current invention are suitable preferably for persons or animals with spontaneous breathing.

Where in embodiments of the present invention reference is made to a flow rate meter, the latter may be a flow rate indicating means that indicates the flow rate in a qualitative manner, as well as a flow rate indicating means that indicates the flow rate in a quantitative manner.

Figure 2:
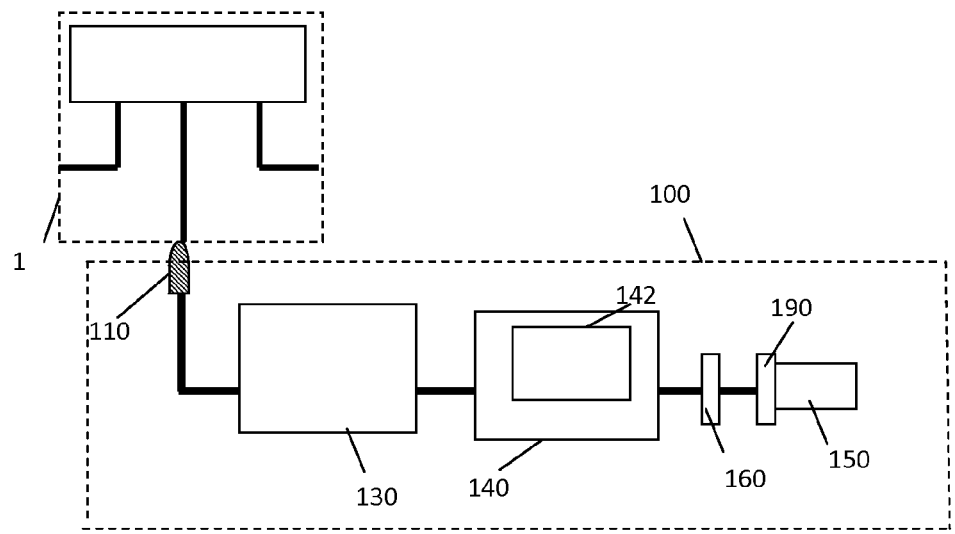
FIG. 2 illustrates a schematic representation of a gas valve according to an embodiment of the present invention in which a regulating system for pulsating flow is in series with a regulating system for continuous flow.
Figure 3:
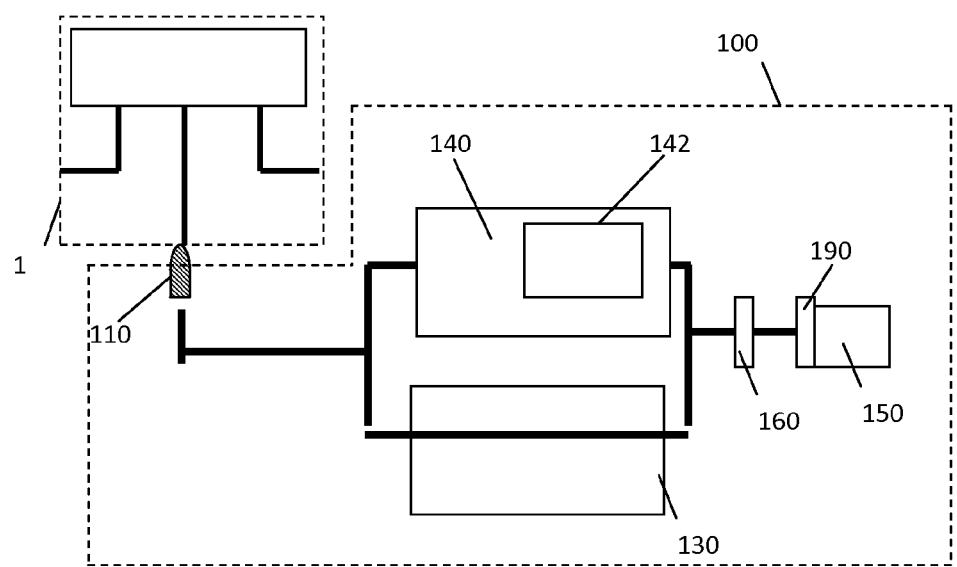

A first aspect of the present invention concerns a gas valve for checking the flow of medical gas. A typical example of administering medical gas to patients is oxygen therapy, although embodiments of the invention are not limited to this. As examples, FIG. 1, FIG. 2 and FIG. 3 show schematic representations of sample gas valves, although embodiments of the present invention are not limited to this. Gas valve 100 according to embodiments of the current invention includes a connection component 110 to connect gas valve 100 to an external supply. Such an external supply can be an external supply network 1 for medical gases at a pressure lower than 50 bars (e.g., 10 bars or lower). It is an advantage that gas valves are provided for specific applications in supply networks such as in hospitals. Alternatively, connection component 110 can be adjusted to connect to a gas canister or gas cylinder at a pressure higher than 50 bars (e.g., approx. 200 bars). Such cylinders enable an uninterrupted supply of oxygen during oxygen therapy in case the patient is moved from one department to another. The disadvantage is that consumption must be monitored so that the cylinders are replaced on time. In a hospital environment, the same problems occur when using cylinders as when using a supply network: need for a simple switch in therapy due to a change in patients or even a switch in therapy of the same patient, autonomy, consumption, need for supplying high flow rates, etc. In embodiments according to the current invention, connection component 110 can be adjusted to correspond with typical connections in the supply network. This can be a connection of a shape laid down in the law, for example, according to DIN norms, CARBA norms, BOC norms or AFNOR norms. It should be clear that the precise type of an installed connection is not limited to embodiments of the current invention. For example, such an external supply network 1 can be a network for distributing medical gases in a hospital and can supply such a medical gas at a pressure in the range of 3.3 bars up to 5.5 bars or similar. A commonly found gas supply network 1, which one finds in hospitals, is the facility of oxygen connections for patients in each room. In a specific embodiment of the current invention, the connection component is equipped with a special geometry that fits a connection to a specific gas supply network eliminating any errors between different gas supply networks. Gas valve 100 according to embodiments of the current invention also includes the regulating system 120. This system is configured to select and supply a pulsating or continuous flow of medical gas. Regulating system 120 also includes flow rate regulator 142 for setting the flow rate of the continuous flow. Flow rate regulator 142 enables regulating or setting the flow rate of the continuous flow. In some embodiments, flow rate regulator 142 is a flow rate meter i.e., a device that measures the flow rate quantitatively. Flow rate regulator 142 can be equipped to select a flow rate out of a set of pre-determined flow rates and/or can be equipped to enable a continuous selection of the flow rate. Selecting a pulsating flow of medical gas can mean a substantial saving in the quantity of medical gas used (e.g., oxygen) without impacting the quality of the therapy. Furthermore, using a pulsating flow has the essential advantage that it is more comfortable for the patient. Continuous medical gas administration (for example, oxygen administration) causes dryness of the nasal membrane, pharynx and oral cavity. Some hospitals use a moisturizer to solve this problem but, in the last years, this is no longer recommended due to the higher infection risk. Using pulsating administration, the drying up of the nasal membrane is minimal, which increases the patient's comfort. In other words, the moisture balance in the nose, pharynx and oral cavity is retained better by using the pulsating technology instead of the continuous technology, resulting in more comfort for the patient.

On the other hand, medical personnel want to use continuous gas flow with high flow rates at various critical moments such as in case of resuscitation or after a fall. In addition, continuous supply of medical gas can also be necessary if the pulsating supply is based on nasal inhalation (e.g., creation of underpressure, measured via a nasal cannula) and if the patient cannot cope with this type of inhalation. Approx. 20% of the patients show mixed breathing (sometimes through the mouth, sometimes through the nose). Furthermore, some people are too confused so that they do not understand that nasal inhalation is necessary for oxygen therapy, for example. Another situation in which pulsating flow of medical gas is not always advised is when using gas valves that are relatively noisy. The pulsating dosage in existing gas valves delivers a bolus of medical gas when the patient inhales. This produces a light puffing noise. Usually, this light puff is not a problem during the daytime, but some patients are sensitive to this noise when trying to fall asleep. Furthermore, a flow rate higher than 6 l/min is often needed, which in some embodiments of the current invention can only be administered in continuous mode. Therefore, continuous gas flow might be necessary for these people or in these situations. Gas valve 100 according to embodiments of the current invention includes therefore flow rate regulator 142 in order to enable selecting the flow rate in case of continuous administration. If supply of medical gas is critical, an accurate administration and as a result, creating an accurate flow is advantageous. Therefore, flow rate regulator 142 can be a flow rate meter in some embodiments. Regulating system 120 in gas valve 100 according to embodiments of the current invention enables you to easily and efficiently select a pulsating or a continuous gas flow.

The advantage of gas valves 100 according to embodiments of the current invention is that they enable a simple selection setting. This makes it better for medical personnel who often are in a busy and stress-inducing environment in which they have to perform many tasks.

An additional advantage of embodiments according to the current invention is that gas valves 100 can easily switch from continuous to pulsating settings and vice versa. This design can be used in hospitals for all kinds of patients and in all types of circumstances. As indicated above, various circumstances sometimes require changes: not only changes between patients, but also a different type of therapy needed for the same patient. For example, the condition of a patient can sometimes improve during his/her stay in the hospital and it can sometimes deteriorate, resulting in the need to adjust the oxygen therapy (usually less oxygen is administered as the patient's condition improves).

In addition, gas valve 100 according to embodiments of the current invention has a lead-through 150 (also referred to as an outlet) for connecting a system to lead the generated gas flow to the patient. A classic example of such a system is a nasal cannula. Lead-through 150 can be a one-channel or a two-channel lead-through (e.g., for connecting a one-channel or two-channel nasal cannula). A two-channel lead-through has two channels in which one channel is used for supplying the medical gas and the other channel is used for detecting the nasal inhalation at a specific moment. The lead-through can have a fitting connection for nasal cannulas available on the market for supplying medical gases to patients. Lead-through 150 can have a specific geometry in a specific embodiment in order to correspond to a specific geometry of the system's connection that supplies the generated gas flow to the patient (e.g., a nasal cannula with a connection of a specific geometry). This will prevent a situation in which the system supplying the generated gas flow to the patient is connected by mistake to the wrong pipeline (e.g., a compressed air pipeline).

In some embodiments, the system can be adjusted to operate with a two-channel nasal cannula and the system used for detecting the nasal inhalation at a specific time can be used to initiate the gas pulse. In other words, the pulse operation can be regulated on the basis of the detected signal.

In other embodiments, the valve is adjusted to operate with a one-channel nasal cannula and the pulse operation is initiated by creating underpressure.

In one embodiment of the valve, a pulsating oxygen supply can occur as follows: A filling space is filled by means of a constant input pressure. A closing port seals off the filling space so that the space stays closed without underpressure. The underpressure, which is generated by the inhalation of the patient (inhalation through the nose), sets the closing port in motion and opens the cavity, resulting in the administration of the gas in the cavity to the patient in a single bolus. In this case, the valve is preferably made in such a way that it closes hermitically if there is no underpressure, and it opens at minimum underpressure created by the nasal inhalation. In general—inherent to the operation—a closing port can be installed to interrupt the pulsating flow if the patient does not generate underpressure by nasal inhalation.

It should be noted that embodiments of the present invention are not limited by the basic principle according to which the pulses are generated in the valve. Generating pulses can occur on the basis of a mechanism according to the current state of technology. In some examples, the pulses can also be generated in valves with a more complex geometry. One example—but not limited to this example—is the pulse generation via multi-stage valves that enable a delicate detection of the inhalation in the first stage and that supply a sufficiently large oxygen pulse by activating the next stages. In addition to more complex geometries, other features such as safety mechanisms can also be built in. One example of such a feature is limiting the number of pulses that are generated, in case the patient starts to hyperventilate. System features for generating pulses are well-known to professionals and therefore, will not be explained in detail here.

According to embodiments of the current invention, regulating system 120 can consist of a first sub-regulating system 130 for supplying a pulsating flow and a second sub-regulating system 140 containing the flow rate regulator 142 for supplying a continuous flow, and a selection is made between the first sub-regulating system 130 and the second sub-regulating system 140. In one embodiment, both sub-regulating systems are in series as illustrated in FIG. 2. This implies that the second sub-regulating system should be open in order to guarantee the proper operation of the sub-regulating system for supplying a pulsating flow. The sequence of the first and the second sub-regulating system can alternate.

In a preferred embodiment, the first sub-regulating system 130 and the second sub-regulating system 140 are in parallel. Such an economical system is shown in FIG. 3. The advantage of this is that the status of the flow rate regulator does not impact the operation of the first sub-regulating system when the valve is set to supply a pulsating flow.

Furthermore, the design of the valve according to embodiments of the current invention can be such that the system in standard setting supplies a pulsating flow spontaneously (e.g., any time a gas flow is started), unless the user selects a continuous flow. In other words, the valve in a preferred embodiment is made in such a way that the standard setting supplies the pulsating flow of medical gas, while the other mode can be obtained via selection. An element can also be provided that—based on a signal—sets the valve in the standard setting in which it supplies a pulsating flow. This element can initiate a standard setting every time the continuous flow is de-activated or if the valve is de-activated. Such an additional element can be controlled pneumatically, mechanically or electronically, and can be based on a detection signal (e.g., using a one-way valve that is installed in the gas valve). In some embodiments, this element can actively prevent the continuous flow, unless an action is performed so that the selection of a continuous flow becomes an active choice. It contributes to the ruggedness and the maintenance-friendliness of the system, if the element is only controlled pneumatically or mechanically, because there is no need to change batteries.

In a preferred embodiment, the valve is based on pneumatic or mechanical operation without electronics to boost the ruggedness.

In some embodiments, an emergency button can be fitted. By pushing this button you select the continuous mode in order to switch quickly to a continuous mode at critical moments such as in case of resuscitation or after a fall.

In a embodiment of the valve in which activating the emergency button triggers a continuous mode, the mechanism for pulsating and/or continuous mode are usually in parallel.

According to embodiments of the current invention, the valve can contain electronic components, although preferably these are made pneumatically and/or mechanically. The pneumatic valves are often more suitable for long-term use in hospitals, for example, because they can be set in a simple manner and because they do not require batteries. Therefore, they can be used for years without requiring additional actions or maintenance. In addition, a significant advantage of not needing power supply is the saving in costs and maintenance time.

Figure 6:
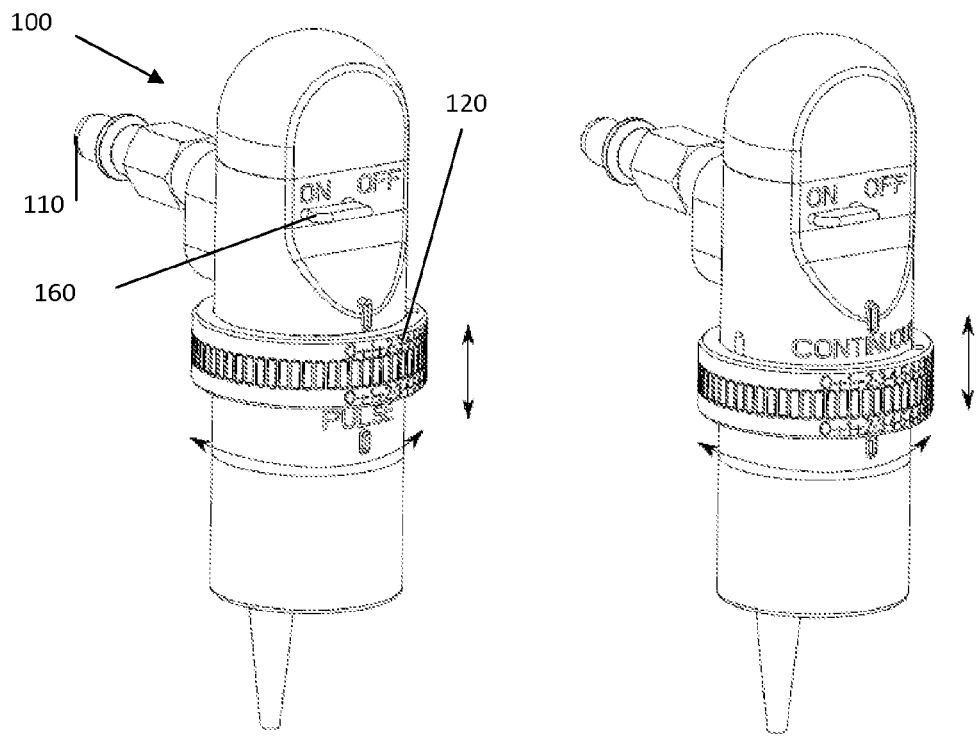
FIG. 6 shows a gas valve according to an embodiment of the present invention in which the flow type and the flow rate can be selected with a single selection element.

In a embodiment of the current invention, the valve can also have one-stage control—possibly including a memory button as described below—so that the entire control can be by operating one selection element. Such a system avoids that the user first needs to set a certain flow in the first selection element and subsequently, needs to set the selected administration mode in another selection element. An example of such a selection element is one that can move in an initial direction in which the flow rate is selected and that can move in a second direction for selecting between pulsating or continuous mode. In one example, the selection element is a selection ring in which the flow rate can be selected by rotating the ring and in which a selection between pulsating and continuous mode is made by shifting the ring in a direction other than the rotating direction. FIG. 6 shows such a selection ring in which (at the left-hand side) a valve is shown that is set to pulsation mode by putting the selection ring in the top position and (at the right-hand side) a valve is shown that is set to continuous mode by shifting the selection ring downwards. This embodiment according to the current invention has the advantage that errors cannot occur (for example, by operating just one of the two selection elements) because the entire selection is made using one and the same selection element.

In another embodiment, the valve can optionally have a closing mechanism 160. This mechanism can close the pulsating and the continuous flow of medical gas (e.g., if the patient is absent or does not use oxygen) and that prevents superfluous flow of medical gas. This closing mechanism can be controlled pneumatically, mechanically, electronically or in any other manner. Closing mechanism 160 can be installed before and after the pulsating and/or continuous mechanism. In another example, this can also be a mechanical On/Off button. Closing system 160 can close automatically if the patient does not utilise medical gas supply and it can be controlled by the detection or the non-detection of any nasal or oral inhalation, etc. This additional closing mechanism can prevent the waste of medical gas. Therefore, the system can have an additional functionality with which the valve will close, but in which the most recently set flow rate is stored in memory. This memory function increases the user-friendliness, also for the oxygen supplier, because he/she does not have to remember the required flow rate in case of not using oxygen temporarily. It also reduces the risk that the oxygen supplier leaves the valve open and causes additional waste.

In certain situations (e.g., emergency situations or for critically ill patients), a specific embodiment can also have a mode, which supplies a continuous flow (independent of the detection of breathing), for a system in which the continuous flow is usually controlled by the presence or absence of breathing in order to prevent waste if the patient is absent. Such a embodiment can have three modes: a pulsating mode triggered by the patient's breathing, a continuous mode in which the breathing is used to check whether the patient uses the system, and a continuous mode independent of the patient's breathing. The latter mode guarantees the supply under all circumstances for critically ill patients.

In a specific embodiment, the valve also has a system cut-off valve 190 (optional), which is activated by disconnecting the system for supplying the gas flow to the patient (e.g., a nasal cannula) in certain cases from lead-through 150. In a case of disconnecting this system (e.g., a nasal cannula), for example, such a system cut-off valve allows you to position a cut-off element in lead-through 150, which prevents the escape of gas. If you connect the system (e.g., a nasal cannula), the connection can enable a switch or movement of the cut-off element, which will open the lead-through 150.

In a specific embodiment of gas valves according to the current invention, the equivalent flow rate that can be obtained via a pulsating gas flow is limited. Most of the time, the current range of available pneumatic metering valves have the equivalent of a maximum pulsating flow rate of 5 l/min. A number of embodiments can dose the equivalent of 6 l/min. In some embodiments according to the current invention, higher medical gas flow rates can also be administered in a pulsating regimen, for example, a flow rate of more than 5 l/min or 6 l/min.

More extensive optimisation that enables pulsating administration with higher flow rates can achieve a lot of saving. In some embodiments, openings and cavities in valves are therefore dimensioned to provide pulsating regimens for higher flow rates. In case of the aforementioned system with automatic opening by means of underpressure, the valve is preferably opened by means of an underpressure of −0.25 to −0.35 cm $H_2O$.

For the purpose of illustration, the following lists the results of a study of 63 patients.

To illustrate the advantages of the embodiments of the current invention, administration using a gas valve with a metering valve is compared with a continuous oxygen administration, and the effect of the oxygen therapy and the calculation of the individual saving factor are determined.

Figure 4:
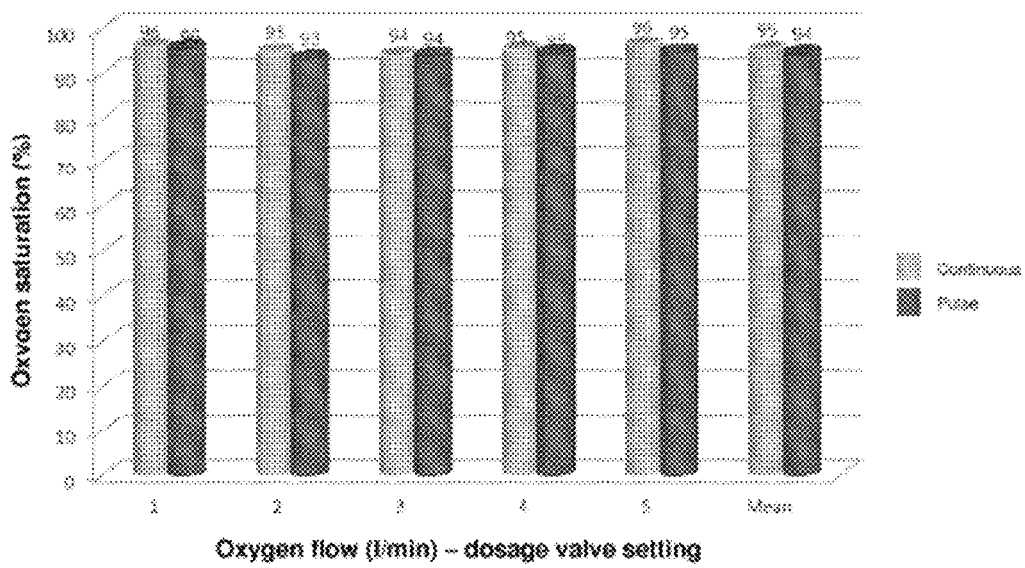
FIG. 4 shows the oxygen saturation achieved for a first set of experiments in using a gas valve according to an embodiment of the present invention.

The study was made using a gas valve with 5 pulsating settings. The pulsating setting 1 of the gas valve is calibrated in such a manner that the administered oxygen bolus has the same effect as 1 l/min continuous oxygen therapy. The pulsating setting 2 of the gas valve is calibrated in such a manner that the administered oxygen bolus has the same effect as 2 l/min continuous oxygen therapy. The pulsating setting 3 of the gas valve is calibrated in such a manner that the administered oxygen bolus has the same effect as 3 l/min continuous oxygen therapy. The pulsating setting 4 of the gas valve is calibrated in such a manner that the administered oxygen bolus has the same effect as 4 l/min continuous oxygen therapy. The pulsating setting 5 of the gas valve is calibrated in such a manner that the administered oxygen bolus has the same effect as 5 l/min continuous oxygen therapy. Five categories of therapies were compared: 1, 2, 3, 4 and 5 l/min of continuous oxygen administration were compared with the metering valve in settings 1, 2, 3, 4 and 5 for pulsating administration. When saturation was measured, each patient got the prescribed continuous flow and subsequently, the equivalent of the pulsating mode (e.g., 3 l/min continuous mode versus setting 3). FIG. 4 shows the average saturation values in continuous mode versus pulsating mode. The light-coloured bars at the left-hand side show the average saturation value with continuous oxygen therapy and the dark-coloured bars at the right-hand side show the average saturation value with pulsating therapy. The saturation values with pulsating therapy compared to the saturation values with continuous therapy did not show significant statistical differences. This illustrates the qualitative oxygen administration that can be achieved with a pulsating system.

Figure 5:
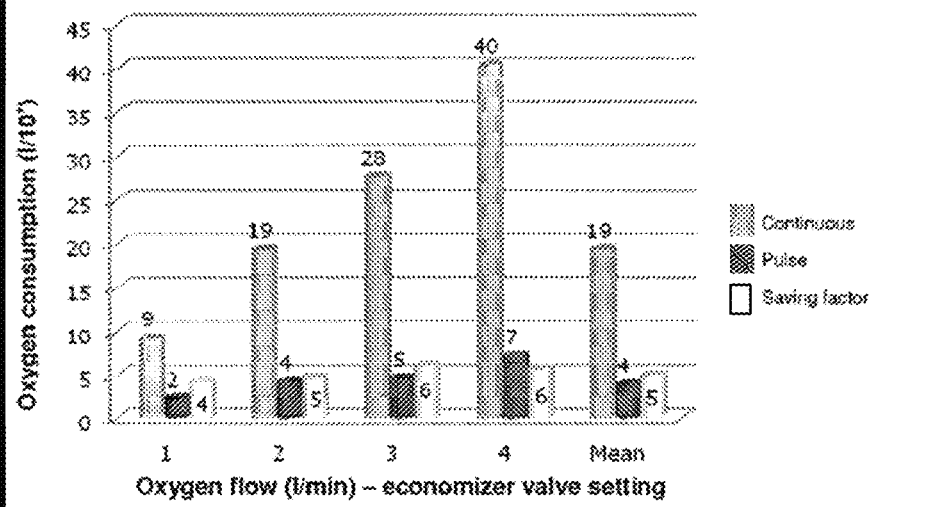
FIG. 5 shows the saving factor for a first set of experiments in using a gas valve according to an embodiment of the present invention.

However, it was determined that the oxygen consumption showed an average decrease by a factor 5 compared to the continuous oxygen flow, while the measuring of saturation values in oxygen therapy did not show a difference. This is illustrated in FIG. 5. The light-coloured bars at the left-hand side show the measured consumption in continuous mode (# of litres in 10 minutes). The dark-coloured bars in the centre show the measured consumption in pulsating mode (# of litres in 10 minutes). The white bars at the right-hand side show the saving factor. It can be deducted from this that pulsating administration that only uses 20% of the oxygen (i.e., 80% oxygen saving) achieves the same therapeutic effect as continuous administration.

In addition—as an experiment for determining the potential saving factor—the valves according to embodiments of the current invention were tested in a surgery ward of low-care cardiology during 4 months. This ward had 26 beds. A mass flow meter and a data logger followed the consumption of the ward over a period of 16 weeks. Furthermore, every change in therapy during the measuring period was carefully recorded. In the odd weeks, the classic system of only continuous flow was used. In the even weeks, the valves according to embodiments of the current invention with the possibility of continuous and pulsating flow were used.

Figure 7:
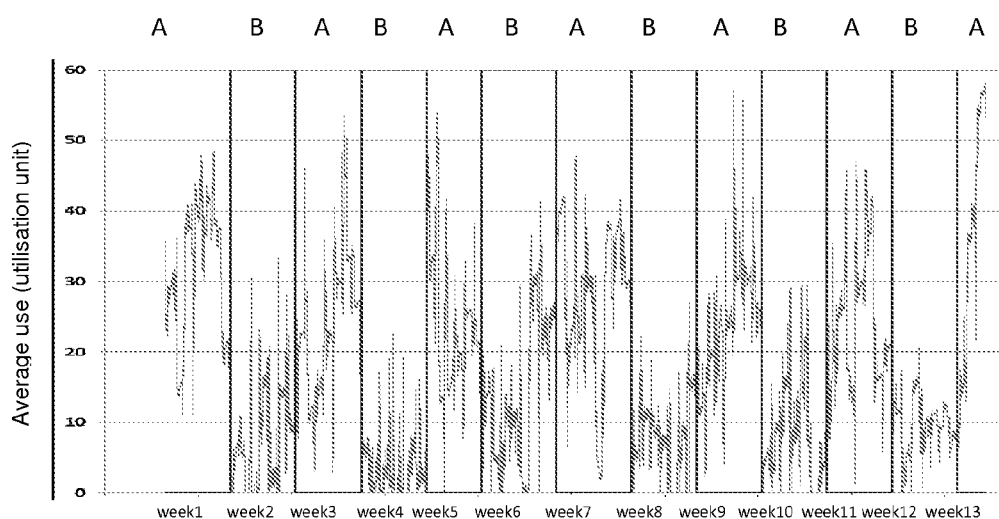
FIG. 7 illustrates the oxygen consumption in a surgery ward when changing utilisation of a gas valve according to an embodiment of the present invention and a gas valve with continuous flow according to the current state of technology.
Figure 8:
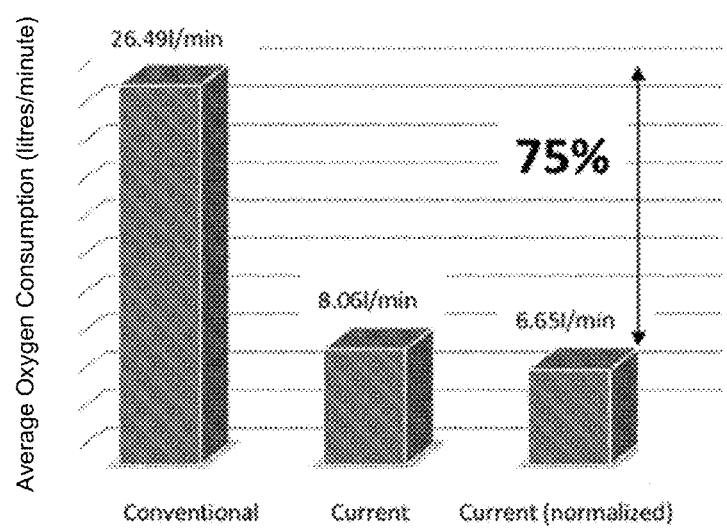
FIG. 8 illustrates the average oxygen consumption when changing utilisation of a gas valve according to an embodiment of the present invention and a gas valve with continuous flow according to the current state of technology.

The results are shown in FIG. 7, which provides an overview of the measured average consumption of the ward during the monitoring period (X-axis), and in FIG. 8, which provides an overview of the average consumption (in litres/minute) of the ward during the periods in which the classic system was used (continuous flow according to the state of technology) and during the periods in which the current system according to the current invention was used (providing the possibility of continuous and pulsating flow). Subsequently, the results of the pulsating system were normalized so that changes in the number of patients and the dosage used did not impact further analysis. It emerges from the time-dependent results of FIG. 7 and from the average consumption of FIG. 8 that a significant oxygen saving was achieved. The recorded average oxygen saving in the measuring period of 4 months was approximately 75%.

Figure 9A:
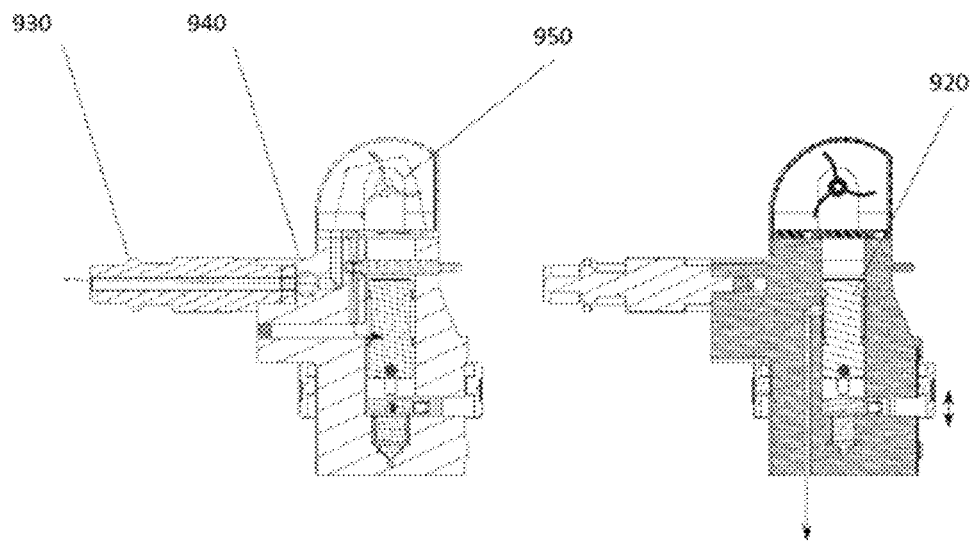
FIG. 9A and FIG. 9B illustrate two cross-sectional views of an internal portion of the gas valve according to an embodiment of the present invention.
Figure 9B:
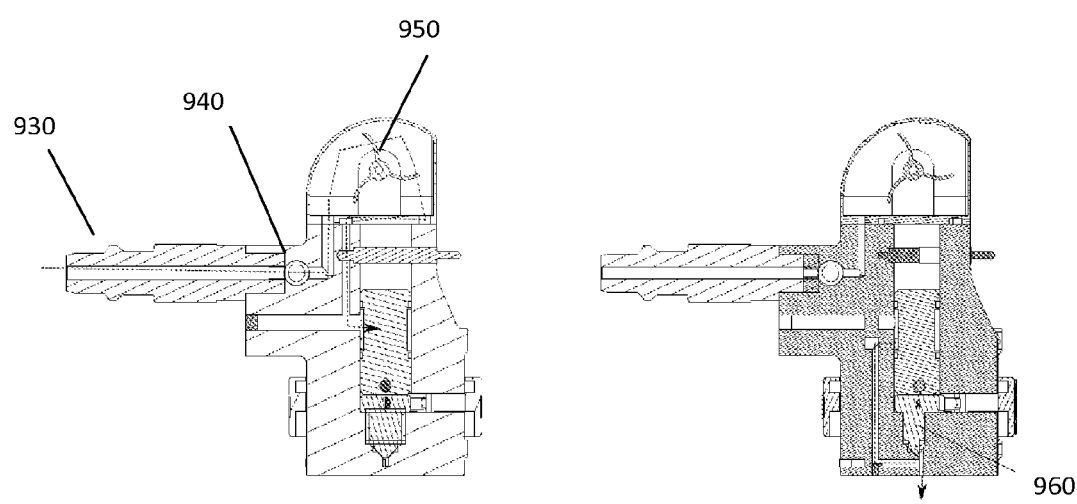

By way of illustration, the inner structure of a gas valve according to an embodiment of the present invention as shown in FIG. 6 is illustrated in FIG. 9a and FIG. 9b, whereby in FIG. 9A two cross-sections are shown of the inner portion of the valve in pulsating supply operation and in FIG. 9B two cross-sections are shown of the inner portion of the valve in continuous supply operation. The inner portion of the pulsating mechanism is not shown in FIG. 9a and FIG. 9b for the gas valve of the current example. The regulating system consists in the present example of a shiftable selection ring, whereby shifting up or down allows selection between pulsating and continuous mode. By rotating the selection ring, a selection further can be made of the preferred flow rate or a flow rate equivalent thereto. Rotation of the selection ring when it is in the downwards position results in control of a needle valve for controlling a continuous supply of medical gas. It is to be noticed that alternatively such control of the continuous supply can also be provided using a different mechanism, such as for example based on flow through calibrated apertures. Rotation of the selection ring when it is in the upward position results in control of the flow rate during pulsating operation. The pulsating mechanism is not shown explicitly in the drawing but can be based on known pulse generating techniques.

The regulating system 120 comprises a selection valve 920—as shown in FIG. 9a—allowing selection between continuous operation and pulsating operation based on positioning of the selection ring.

A quick fitting mechanism 930 also is shown in FIG. 9a, the quick fitting mechanism being a component of the connection component—allowing coupling of the valve to the external supply. A pressure drop regulating system 940 allows a reduction of the input pressure. Furthermore, also the internal structure of the flow rate meter 950 is visible. In FIG. 9b a needle valve 960 also is shown, by which the flow rate of the continuous supply can be provided.

In operation, the medical gas flows from the connection component 110, through the flow rate meter towards an internal portion of the gas valve determined by the selected mode and selected using the selection mechanism, such that the medical gas flow can be converted in a pulsated gas flow or a controlled continuous gas flow. The gas flow—being pulsed or continuous according to the selected mode—is then guided to an outlet for supplying to a patient, typically using a nasal cannula.

The invention claimed is:

1. A gas valve adapted for controlling the flow of a medical gas for oxygen therapy in case of spontaneous breathing, the gas valve comprising a connection component for connecting the gas valve to an external supply;

a regulating system configured for selecting between either a pulsating flow of medical gas or a continuous flow of medical gas to be delivered, and for supplying the pulsating flow of medical gas or the continuous flow of medical gas according to said selecting, the pulsating flow of medical gas being based on underpressure generated by inhalation of the patient, the regulating system comprising a selection element configured to provide selecting between the pulsating flow or the continuous flow, and further configured to provide a selection between different flow rates for the pulsating flow being selectable through the selection element wherein the selection element is a selection ring in which the flow rate for pulsating flow can be selected by rotating the ring;

wherein the regulating system contains a flow rate regulator for controlling a flow rate of the continuous flow of medical gas and supplying the flow rate of the continuous flow of medical gas, and wherein said selecting between the pulsating flow or the continuous flow is provided by movement of the selection ring along a first direction, and selecting the flow rate of the continuous flow of medical gas is provided by movement of the selection ring along a second direction, the second direction being different than the first direction.

2. The gas valve according to claim 1, wherein the flow rate regulator is equipped for at least controllably supplying the selected flow rate of the continuous flow in the range of 2 litres per minute to 8 litres per minute.

3. The gas valve according to claim 1, wherein the flow rate regulator is a flow rate meter.

4. The gas valve according to claim 1, wherein the gas valve is configured so that the flow rate regulator does not affect the flow of medical gas if the regulating system is set to pulsating flow of medical gas.

5. The gas valve according to claim 1, in which the regulating system comprises a first sub-regulating system for supplying a pulsating flow and a second sub-regulating system for supplying a continuous flow, wherein the flow rate regulator is part of the second sub-regulating system and wherein the gas valve is configured so that the first sub-regulating system and the second sub-regulating system are in parallel gas channels.

6. The gas valve according to claim 1, wherein the gas valve is configured so that the regulating system generates a pulsating gas flow at the start of a gas flow.

7. The gas valve according to claim 1, in which the regulating system comprises a first sub-regulating system for supplying the pulsating flow and a second sub-regulating system for supplying the continuous flow, wherein an additional selection system is configured to activate the second sub-regulating system, wherein the additional selection system is de-activated if the continuous flow is interrupted.

8. The gas valve according to claim 1, wherein the gas valve is based on solely mechanical and pneumatic operation.

9. The gas valve according to claim 1, wherein the selection element of the regulating system enables selecting the type of flow via a click mechanism.

10. The gas valve according claim 1, wherein the gas valve is adapted for closing the pulsating flow on the basis of a pre-determined signal.

11. The gas valve according to claim 1, wherein the gas valve comprises a closing mechanism for closing the pulsating and continuous flow on the basis of a pre-determined signal.

12. The gas valve according to claim 1, wherein the gas valve is provided with a one-channel lead-through in order to connect a one-channel nasal cannula for supplying medical gas to a patient or where the gas valve is provided with a two-channel lead-through in order to connect a two-channel nasal cannula for supplying medical gas.

13. The gas valve according to claim 12, wherein the gas valve comprises a system cut-off valve for cutting off the gas flow, which is activated by disconnecting the one-channel nasal cannula or the two-channel nasal cannula from the one-channel lead-through or two-channel lead-through.

14. The gas valve according to claim 1, wherein the flow rate regulator enables the selected flow rate to be more than 15 litres of medical gas per minute.

15. The gas valve according to claim 1, wherein the selection element of the flow rate regulator is adapted to controllably select the flow rate of the continuous supply in a continuous manner.

16. The gas valve according to claim 1, wherein the regulating system is adapted to supply a pulsating flow being equivalent with a continuous flow rate of 6 litres of medical gas per minute.

17. The gas valve according to claim 1, wherein the connection component is adapted to connect the gas valve to an external supply network of medical gases at a pressure lower than 50 bars.

18. The gas valve according to claim 1, wherein the flow rate regulator enables the flow rate to be more than 10 litres of medical gas per minute in continuous flow.

19. A method for controlling a flow of a medical gas for oxygen therapy in case of spontaneous breathing, the method comprising:

connecting, with a connection component, a gas valve to an external supply, the gas valve being adapted to control the flow of the medical gas for the oxygen therapy;

selecting, with a regulating system of the gas valve, between either a pulsating flow of the medical gas or a continuous flow of the medical gas to be delivered, the regulating system comprising a selection element configured to provide said selecting between the pulsating flow or the continuous flow, and further configured to provide a selection between different flow rates for the pulsating flow being selectable through the selection element, wherein the selection element is a selection ring in which the flow rate for pulsating flow can be selected by rotating the ring; and supplying, with the regulating system, the pulsating flow of medical gas or the continuous flow of medical gas according to said selecting, wherein the pulsating flow of the medical gas is based on underpressure generated by inhalation of a patient, wherein the regulating system contains a flow rate regulator for controlling a flow rate of the continuous flow of medical gas and supplying the flow rate of the continuous flow of the medical gas, and wherein said selecting between the pulsating flow or the continuous flow is provided by movement of the selection ring along a first direction, and selecting the flow rate of the continuous flow of medical gas is provided by movement of the selection ring along a second direction, the second direction being different than the first direction.

20. The method according to claim 19, wherein the flow rate regulator enables the flow rate of the continuous flow of to be more than 10 litres of medical gas per minute.

\* \* \* \* \*